US008506501B2

(12) United States Patent
Fu

(10) Patent No.: US 8,506,501 B2
(45) Date of Patent: Aug. 13, 2013

(54) LIGHTWEIGHT WHEEZE DETECTION METHODS AND SYSTEMS

(75) Inventor: Yongji Fu, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 710 days.

(21) Appl. No.: 12/661,477

(22) Filed: Mar. 18, 2010

(65) Prior Publication Data
US 2011/0230777 A1    Sep. 22, 2011

(51) Int. Cl.
  *A61B 5/08*    (2006.01)
(52) U.S. Cl.
  USPC ........................................................ 600/529
(58) Field of Classification Search
  USPC ......................................... 600/586, 529–543
  See application file for complete search history.

(56) References Cited

U.S. PATENT DOCUMENTS

| | | | | |
|---|---|---|---|---|
| 5,165,417 A | * | 11/1992 | Murphy, Jr. | 600/529 |
| 6,261,238 B1 | * | 7/2001 | Gavriely | 600/532 |
| 2006/0198533 A1 | | 9/2006 | Wang et al. | 381/67 |
| 2006/0243280 A1 | | 11/2006 | Caro | 128/204.23 |
| 2007/0010722 A1 | | 1/2007 | Suzuki et al. | |
| 2007/0118054 A1 | | 5/2007 | Pinhas et al. | 600/587 |
| 2007/0287896 A1 | | 12/2007 | Derchak et al. | |
| 2009/0137918 A1 | * | 5/2009 | Noffsinger et al. | 600/529 |
| 2009/0171231 A1 | * | 7/2009 | Caro et al. | 600/529 |
| 2009/0248336 A1 | * | 10/2009 | Afgani et al. | 702/69 |
| 2011/0125044 A1 | * | 5/2011 | Rhee et al. | 600/534 |

FOREIGN PATENT DOCUMENTS

JP    2006-167427    6/2006

OTHER PUBLICATIONS

Jain, et al. "Lung Sound Analysis for Wheeze Episode Detection," Engineering in Medicine and Biology Society, 2008. EMBS 2008. 30th Annual International Conference of the IEEE, pp. 2582-2585.*
N. Meslier et al, "Wheezes," Eur Respir J, 1995, 8, 1942-48.
A. Homs-Corbera et al., "Algorithm for Time-Frequency Detection and Analysis of Wheezes," Proc of the 22nd Ann EMBS Intl Conf, Jul. 23-28, 2000, Chicago, IL.
T. Fenton et al, "Automated Spectral Characterization of Wheezing in Asthmatic Children," IEEE Trans on Bio Eng, vol. BME-32, No. 1, Jan. 1985.
Y. Qiu et al, "Automatic Wheeze Detection Based on Auditory Modelling," Proc IMechE vol. 219 Part H: J Eng in Medicine, 219-27, 2005.
S. Taplidou et al, "Wheeze Detection Based on Time-Frequency Analysis of Breath Sounds," Comp in Bio and Medicine 37, 2007, 1073-83.

* cited by examiner

*Primary Examiner* — Navin Natnithithadha
*Assistant Examiner* — Eric Messersmith
(74) *Attorney, Agent, or Firm* — Scot A. Reader

(57) ABSTRACT

Lightweight wheeze detection methods and systems for portable respiratory health monitoring devices conserve computing resources in portable respiratory health monitoring devices by employing lightweight algorithm that calculates a partial STFT image of a respiratory signal that includes all data points necessary for wheeze detection but excludes many data points that are unnecessary for wheeze detection. The methods and systems provide substantial savings in computing resources while still ensuring every wheeze in a respiratory signal is detected.

18 Claims, 5 Drawing Sheets

LIGHTWEIGHT WHEEZE DETECTION METHODS AND SYSTEMS

BACKGROUND OF THE INVENTION

The present invention relates to ambulatory health monitoring and, more particularly, to lightweight wheeze detection methods and systems designed to improve portable respiratory health monitoring devices.

Wheeze monitoring is an important aspect of chronic respiratory disease management, such as asthma management. Wheezes are adventitious lung sounds that are superimposed on normal breath sounds and indicate constricted breathing. A wheeze is generally characterized by a high pitch sound lasting a predetermined duration, and can be detected by evaluating time and frequency components of a respiratory signal.

In conventional wheeze monitoring, a complete short-time Fourier transform (STFT) image is calculated to detect wheezes in a respiratory signal. The complete STFT image provides a two-dimensional representation of the amplitude of the respiratory signal for all data points in a time and frequency domain according to the well-known formula $$STFT\{x(t)\} \equiv X(\tau, \omega) = \int_{-\infty}^{\infty} x(t)w(t-\tau)e^{-j\omega t}dt$$

where w(t) is the window function, x(t) is the signal to be transformed and $X(\tau,\omega)$ is the Fourier transform of $x(t)w(t-\tau)$, a complex function representing the phase and magnitude of the signal over time and frequency. Wheezes can be detected from evaluation of selected data points in the complete STFT image.

Conventional wheeze monitoring is not well-suited for portable respiratory health monitoring devices that continually acquire and evaluate a respiratory signal as a person wearing the system goes about his or her daily life. Such devices have limited computing resources, and calculating a complete STFT image to detect wheezes often consumes an unacceptably large share those scarce resources.

SUMMARY OF THE INVENTION

The present invention provides lightweight wheeze detection methods and systems for portable respiratory health monitoring devices. The invention conserves computing resources in portable respiratory health monitoring devices by employing a lightweight algorithm that calculates a partial STFT image of a respiratory signal that includes all data points that are necessary for wheeze detection but excludes many data points that are unnecessary for wheeze detection. The methods and systems provide substantial savings in computing resources while still ensuring every wheeze in a respiratory signal is detected.

In one aspect of the invention, a lightweight wheeze detection method comprises the steps of receiving by a respiratory data processing system a respiratory signal; calculating by the processing system noncontiguous lines of a STFT image of the respiratory signal until a start line conforming to one or more wheeze peak criteria is identified; once a start line conforming to the wheeze peak criteria is identified, calculating by the processing system contiguous lines of the STFT image preceding the start line and contiguous lines of the STFT image following the start line until both a preceding line and a following line not conforming to the wheeze peak criteria are identified; and, once both a preceding line and a following line not conforming to the wheeze peak criteria are identified, determining by the processing system using a total count of calculated lines of the STFT image conforming to the wheeze peak criteria whether a duration of a peak conforms to one or more wheeze duration criteria.

In some embodiments, the wheeze peak criteria comprise minimum peak frequency, minimum peak height and minimum peak width.

In some embodiments, conformance of a calculated line of the STFT image to the wheeze peak criteria is identified upon detecting that frequency, height and width of a highest amplitude peak in the calculated line exceed predetermined frequency, height and width thresholds, respectively.

In some embodiments, nonconformance of a calculated line of the STFT image with the wheeze peak criteria is identified upon detecting that one or more of frequency, height or width of a highest amplitude peak in the calculated line is below a predetermined frequency, height or width threshold, respectively.

In some embodiments, the wheeze duration criteria comprise a minimum wheeze duration.

In some embodiments, conformance to the wheeze duration criteria is determined based at least in part on a comparison of the total count with a predetermined wheeze duration threshold.

In some embodiments, each consecutive pair of the noncontiguous lines is separated by a predetermined number of lines of the STFT image determined in accordance with a minimum wheeze duration.

In some embodiments, the second calculating step comprises limiting by the processing system calculation of the contiguous lines preceding the start line and the contiguous lines following the start line to a region of each contiguous line that is within a predetermined range of a frequency of a highest amplitude peak of the start line.

In some embodiments, the method further comprises, upon determining that the duration conforms to the wheeze duration criteria, the step of calculating by the processing system a wheeze rate.

In some embodiments, the method further comprises, upon determining that the duration does not conform to the wheeze duration criteria, the steps of skipping by the processing system a predetermined number of lines of the STFT image determined in accordance with a minimum wheeze duration and re-performing the first calculating step.

In another aspect of the invention, an ambulatory health monitoring device comprises a respiratory data capture system; a respiratory data acquisition system communicatively coupled with the capture system; a respiratory data processing system communicatively coupled with the acquisition system; and a respiratory data output interface communicatively coupled with the processing system, wherein the processing system receives a respiratory signal from the capture system via the acquisition system, calculates noncontiguous lines of a STFT image of the respiratory signal until a start line conforming to one or more wheeze peak criteria is identified, once a start line conforming to the wheeze peak criteria is identified, calculates contiguous lines of the STFT image preceding the start line and contiguous lines of the STFT image following the start line until both a preceding line and a following line not conforming to the wheeze peak criteria are identified, once both a preceding line and a following line not conforming to the wheeze peak criteria are identified, determines using a total count of calculated lines of the STFT image conforming to the wheeze peak criteria whether a duration of a peak conforms to one or more wheeze duration criteria, upon determining that the duration conforms to the wheeze duration criteria, calculates a wheeze rate and transmits information indicative of the wheeze rate to the output interface.

In some embodiments, the wheeze peak criteria comprise minimum peak frequency, minimum peak height and minimum peak width.

In some embodiments, conformance of a calculated line of the STFT image to the wheeze peak criteria is identified upon detecting that frequency, height and width of a highest amplitude peak in the calculated line exceed predetermined frequency, height and width thresholds, respectively.

In some embodiments, nonconformance of a calculated line of the STFT image with the wheeze peak criteria is identified upon detecting that one or more of frequency, height or width of a highest amplitude peak in the calculated line is below a predetermined frequency, height or width threshold, respectively.

In some embodiments, the wheeze duration criteria comprise a minimum wheeze duration.

In some embodiments, conformance of the duration to the wheeze duration criteria is determined based at least in part on a comparison of the total count with a predetermined wheeze duration threshold.

In some embodiments, each consecutive pair of the noncontiguous lines is separated by a predetermined number of lines of the STFT image determined in accordance with a minimum wheeze duration.

In some embodiments, the processing system limits calculation of the contiguous lines preceding the start line and the contiguous lines following the start line to a region of each contiguous line that is within a predetermined range of a frequency of a highest amplitude peak of the start line.

In yet another aspect of the invention, a lightweight wheeze detection method comprises the steps of receiving by a respiratory data processing system a respiratory signal; calculating by the processing system a partial STFT image of the respiratory signal comprising selected data points of selected lines of a complete STFT image of the respiratory signal, wherein the lines and the data points are selected by the processing system based at least in part on one or more wheeze peak criteria; and detecting by the processing system a wheeze in the partial STFT image based at least in part on the wheeze peak criteria.

In some embodiments, the lines are selected and the wheeze is detected by the processing system based at least in part on one or more wheeze duration criteria.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
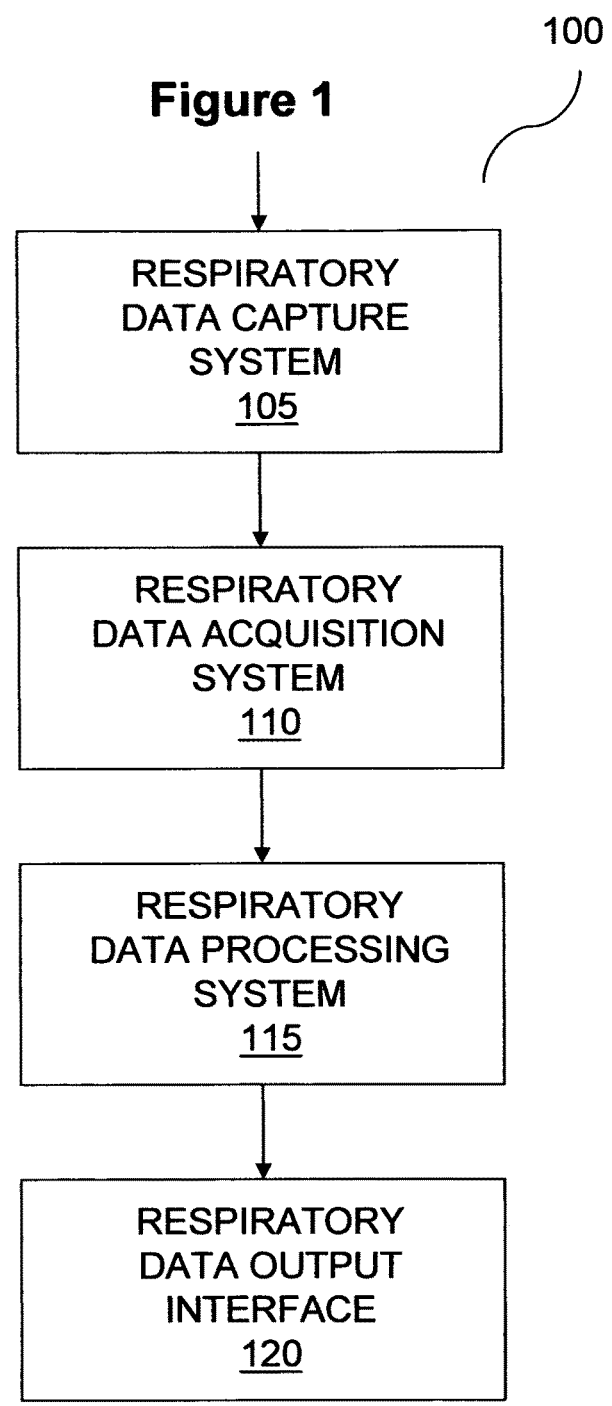
FIG. 1 shows an ambulatory health monitoring device in some embodiments of the invention.

FIG. 1 shows an ambulatory health monitoring device 100 in some embodiments of the invention. Monitoring device 100 includes a respiratory data capture system 105, a respiratory data acquisition system 110, a respiratory data processing system 115 and a respiratory data output interface 120 communicatively coupled in series.

Capture system 105 detects lung sounds at a detection point, such as a trachea, chest or back of a person being monitored and transmits a respiratory signal to acquisition system 110 in the form of an electrical signal generated from detected lung sounds. Capture system 105 may include, for example, a sound transducer positioned on the body of a human subject.

Acquisition system 110 amplifies, filters, performs analog/digital (A/D) conversion and automatic gain control (AGC) on the respiratory signal received from capture system 105, and transmits the respiratory signal to processing system 115. Amplification, filtering, ND conversion and AGC may be performed by serially arranged pre-amplifier, band-pass filter, final amplifier, ND conversion and AGC stages, for example.

Processing system 115, under control of a processor executing software instructions, performs time and frequency domain processing, including calculation of partial STFT images, on the respiratory signal to detect wheezes and calculate wheeze rate. Processing system 115 under control of the processor outputs the wheeze rate to data output interface 120.

Data output interface 120 includes one or more of a user interface, a local analysis module, a data management element and a network interface for displaying, processing, storing and/or transmitting information received from processing system 115, such as wheeze rate.

While in the illustrated embodiment capture system 105, acquisition system 110, processing system 115 and data output interface 120 are part of a portable (e.g. wearable) ambulatory health monitoring device that monitors a person's physiological well-being in real-time as the person performs daily activities, in other embodiments capture system 105, acquisition system 110, processing system 115 and/or data output interface 120 may be part of separate devices that are remotely coupled via wired or wireless links.

Figure 2:
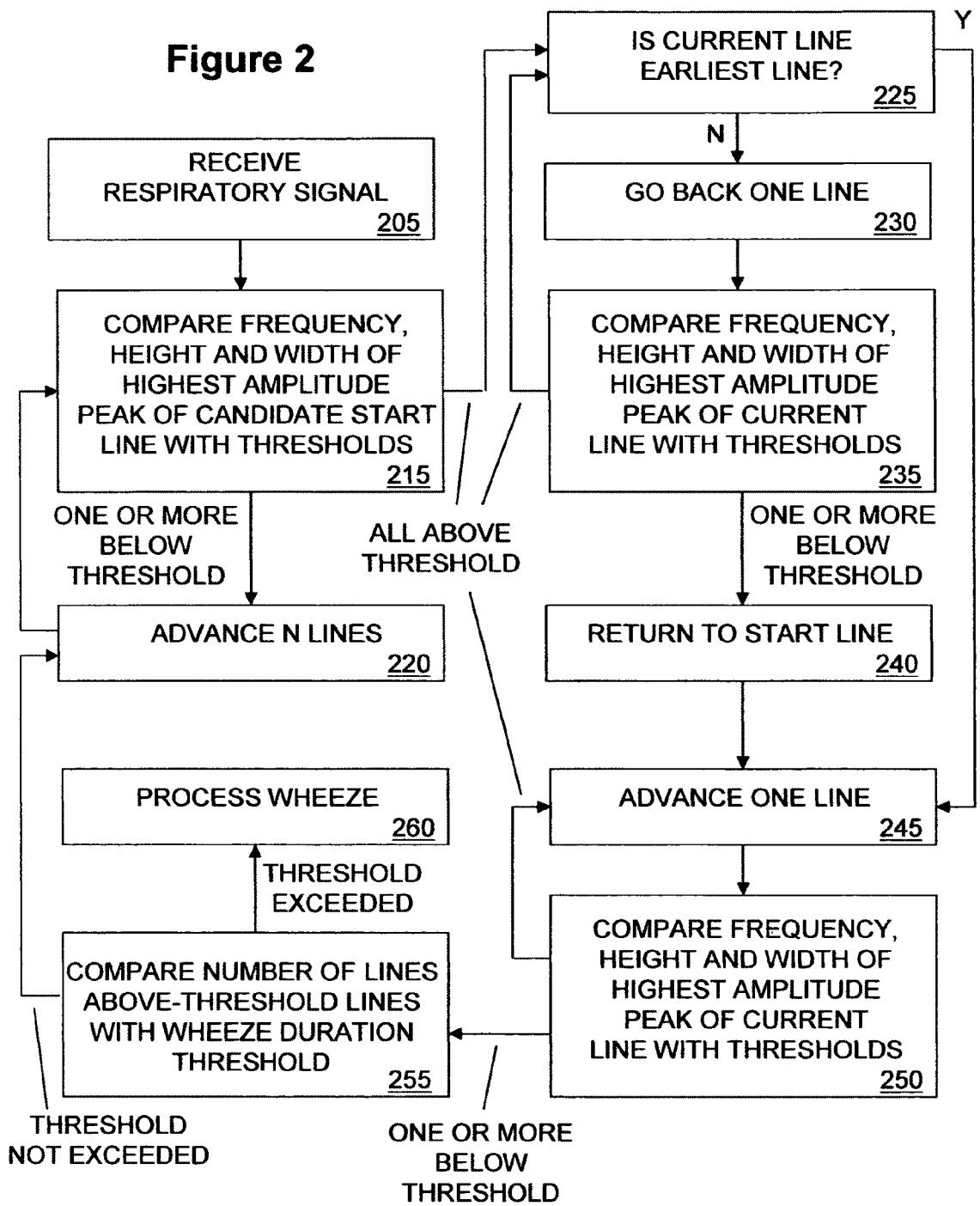
FIG. 2 shows a wheeze detection method performed by a respiratory data processing system in some embodiments of the invention.

FIG. 2 shows a wheeze detection method performed by processing system 115 in some embodiments of the invention under control of a processor that executes software instructions. The method will be described in conjunction with FIGS. 3-7.

Figure 3:
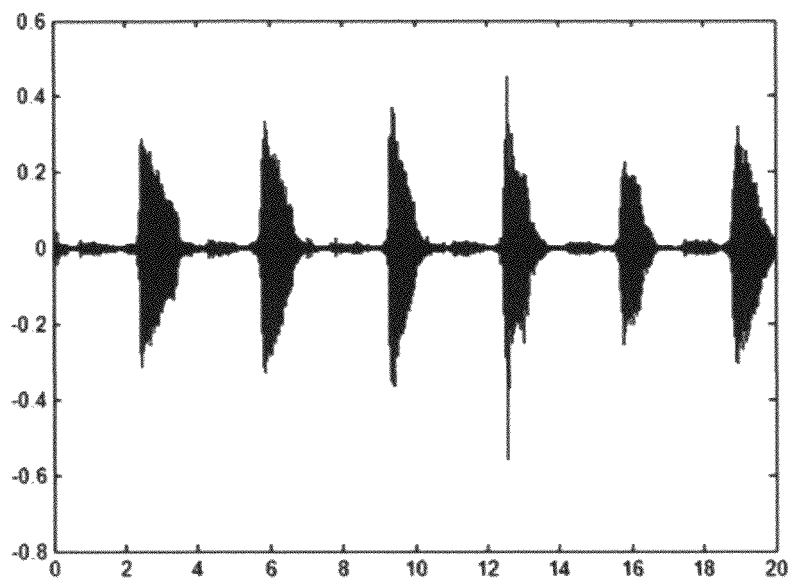
FIG. 3 shows a respiratory signal received by a respiratory data processing system.

Initially, processing system 115 receives a time domain respiratory signal from acquisition system 110 (205). FIG. 3 shows an exemplary time domain respiratory signal received by a processing system 115. The x-axis of the respiratory signal is time in seconds and the y-axis of the respiratory signal is sound amplitude in arbitrary units. The respiratory signal exhibits periodicity corresponding to a respiratory cycle (i.e. inhale/exhale). Wheezes are not readily detectable in the time domain respiratory signal.

Next, processing system 115 calculates noncontiguous lines of an STFT image of the respiratory signal until a start line conforming to wheeze peak criteria is identified. In this regard, processing system 115 compares the frequency, height and width of the highest amplitude peak of a candidate start line of an STFT image with predetermined frequency, height and width thresholds, respectively (215). If the frequency, height and width of the highest amplitude peak of the candidate start line are all above threshold, the candidate start line is chosen as the start line and the flow moves to Step 225. On the other hand, if one or more of the frequency, height or width of the highest amplitude peak of the candidate start line is below threshold, processing system 115 advances N lines from the candidate start line and re-performs Step 215 at the new candidate start line. Steps 215 and 220 are repeated in loop until a start line is chosen or all candidate start lines have been calculated and found wanting.

Figure 4:
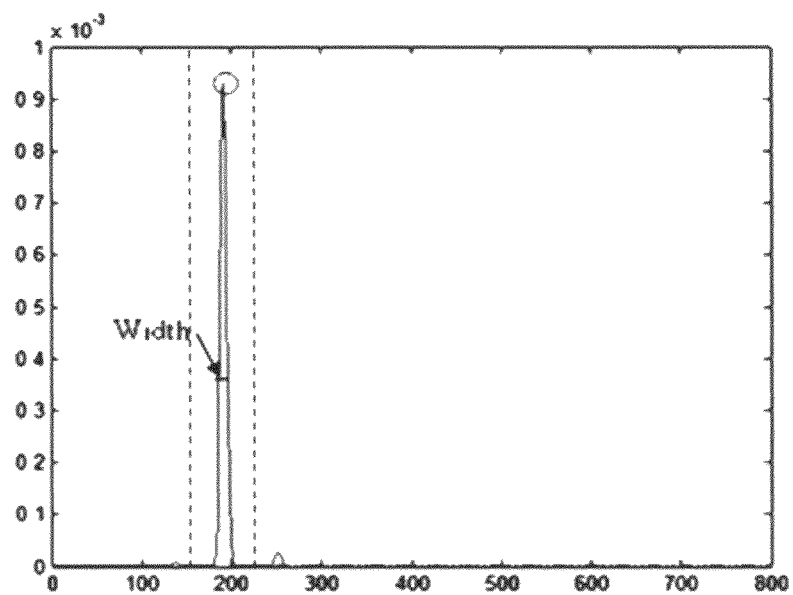
FIG. 4 shows a line of a STFT image calculated by a respiratory data processing system.

To better illustrate, FIG. 4 shows a line of an STFT image calculated by processing system 115. The line is a slice of a complete STFT image taken over a short time window of size W. The x-axis of the line is frequency in hertz and the y-axis of the line is amplitude in arbitrary units. The highest amplitude peak in the line is centered at about 190 Hz. In Step 215, the frequency, height and width of the peak are compared with frequency, height and width thresholds, respectively, to determine whether the line is chosen as the start line. By way of example, a frequency threshold may be set at 150 Hz to conform to a minimum frequency required for a peak to be properly classified as a wheeze. Since the frequency of the peak shown in FIG. 4 is greater than 150 Hz, the frequency threshold would be surpassed in this example. Similar comparisons would be made between the height of the peak (indicated by the circle in FIG. 4) and the width of the peak (indicated in FIG. 4) and minimum height and width thresholds characteristic of a wheeze to determine whether the line is chosen as the start line.

The value of N used in Step 220 is judiciously selected to correspond to a minimum duration required for a peak to be properly classified as a wheeze. By selecting a value for N that conforms to a wheeze of minimum duration, the total number of lines calculated by processing system 115 is reduced by up to a factor of N as compared with wheeze detection methods that calculate a complete STFT image. Moreover, this reduction in calculations is realized without risking failure to detect any wheeze expressed in the respiratory signal. More particularly, the value of N may be determined according to the formula $$N = D / [W(1-X)]$$

where D is the minimum wheeze duration, W is the window size of each STFT line and X is the percentage of overlap between adjacent STFT lines. By way of example, D may be configured as 250 ms, W may be configured as 80 ms and X may be configured as 0.50, such that the formula yields N=6, after rounding.

Once the start line has been chosen, processing system 115 calculates contiguous lines preceding the start line until a preceding line not conforming to the wheeze peak criteria is identified. In this regard, processing system 115 first checks whether the current line, which is initially the start line, is the earliest available line of the STFT image (225). If the current line is the earliest available line, calculation of preceding lines is not possible and the flow moves to Step 245. On the other hand, if the current line is not the earliest available line, calculation of preceding lines is possible and processing system 115 moves back one line (230) and compares the frequency, height and width of the highest amplitude peak of the new current line with predetermined frequency, height and width thresholds, respectively (235). If one of the frequency, height and width of the highest amplitude peak of the current line is below threshold, the flow moves to Step 240. On the other hand, if all of the frequency, height or width of the highest amplitude peak of the current line are above threshold, processing system 115 returns to Step 225. Steps 225-235 are repeated in loop until a line preceding the start line is found to not conform to the wheeze peak criteria or all available lines preceding the start line have been calculated and found to conform.

Next, processing system 115 calculates contiguous lines following the start line until a following line not conforming to the wheeze peak criteria is identified. In this regard, processing system 115 advances to the first line after the start line (240, 245) and compares the frequency, height and width of the highest amplitude peak of the current line with the frequency, height and width thresholds, respectively (250). If one of the frequency, height and width of the highest amplitude peak of the current line is below threshold, the flow moves to Step 255. On the other hand, if all of the frequency, height or width of the highest amplitude peak of the current line are above threshold, processing system 115 returns to Step 245. Steps 245 and 250 are repeated in loop until a line following the start line is found to not conform to the wheeze peak criteria.

Naturally, the order in which processing system 115 calculates contiguous lines preceding and following the start line is reversible. That is, processing system 115 may first calculate contiguous lines following the start line and thereafter calculate contiguous lines preceding the start line.

Importantly, calculation of the contiguous lines preceding and following the start line is limited to a region of each contiguous line within a predetermined range of a central frequency of the highest amplitude peak of the start line. For example, if the line of FIG. 4 is chosen as the start line, processing system 115 limits calculation of each contiguous line preceding and following the start line to data points bounded by the dotted lines shown in FIG. 4. This limitation provides additional significant reduction in the number of data points of the STFT image calculated by processing system 115 as compared to methods that calculate the complete STFT image.

Once both a preceding line and a following line not conforming to the wheeze peak criteria are identified, processing system 115 determines using the total count of calculated lines conforming to the wheeze peak criteria whether the duration of the highest amplitude peak conforms to a wheeze duration criterion. In this regard, processing system 115 compares the total number of above-threshold lines calculated attendant to performing Steps 215, 235 and 250 with a wheeze duration threshold (255). In some embodiments, the total count is compared directly with a wheeze duration threshold that is expressed as a number of lines (e.g. N=6). In other embodiments, the total count is converted to a duration in units of time and the duration is compared with a wheeze duration threshold that is expressed in units of time. In either event, if the comparison is below threshold, the duration of the peak conforming to the wheeze peak criteria is insufficient to classify the peak as a wheeze, and the flow returns to Step 220. On the other hand, if the comparison is above threshold, the duration of the peak is sufficient to classify the peak as a wheeze, and processing system 115 processes the wheeze (260). Wheeze processing may include, for example, calculating a wheeze rate according to the formula $$R = t_w / t_{tot}$$

where R is the wheeze rate, $t_w$ is the duration of the wheeze, and $t_{tot}$ is the duration of a respiratory cycle.

Figure 5:
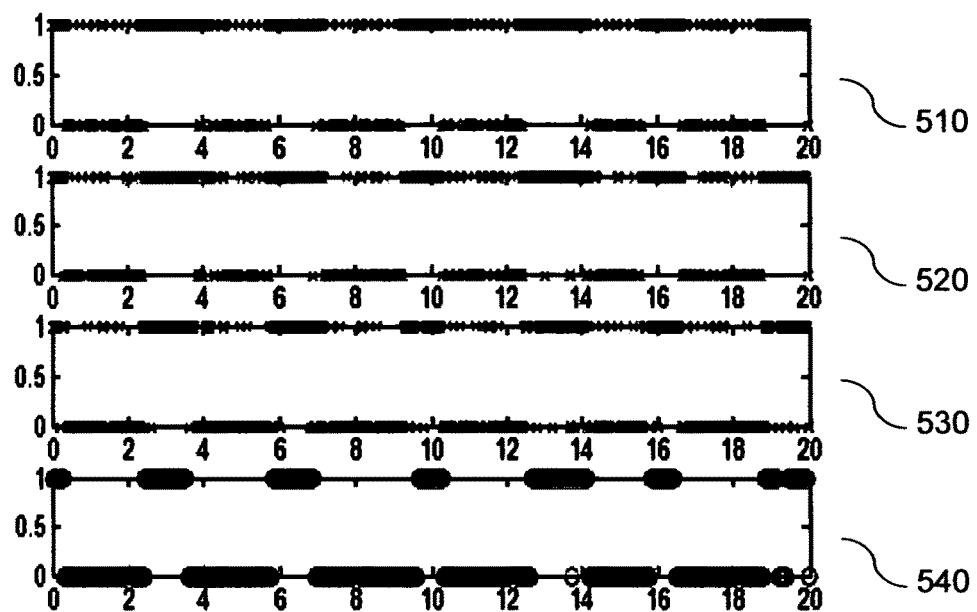
FIG. 5 shows binary values of wheeze detection parameters calculated by a respiratory data processing system.

FIG. 5 shows exemplary binary values of wheeze detection parameters determined by processing system 115 attendant to performing the method of FIG. 2. Values of "1" indicate conformance with a given criterion and values of "0" indicate nonconformance with a given criterion. FIG. 5 shows values for the following criteria: peak height 510, peak width 520, peak contiguity 530 (i.e. whether the peak height and peak width criteria are satisfied for both the preceding line and the current line) and wheeze detection 540 (i.e. whether peak contiguity persists over a minimum wheeze duration).

Figure 6:
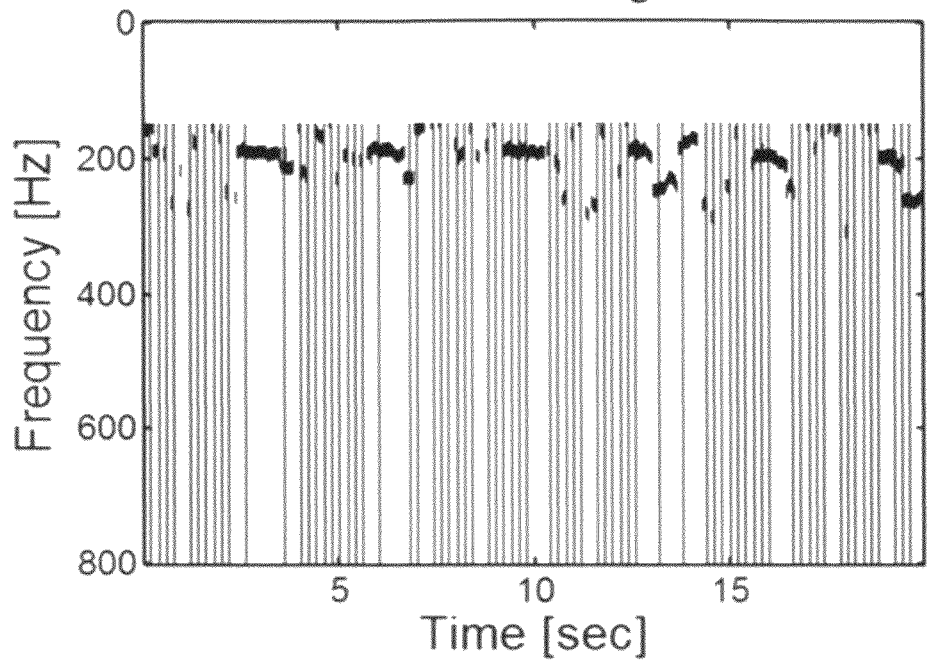
FIG. 6 is a map showing selected data points of a STFT image calculated by a respiratory data processing system.

FIG. 6 is a map showing selected data points of a STFT image of the respiratory signal calculated by processing system 115 attendant to performing the method of FIG. 2. Dark areas of the map indicate data points that were calculated. Light areas of the map indicate data points that were not calculated, and reflect calculation savings relative to methods wherein the complete SFTF image is calculated.

Figure 7:
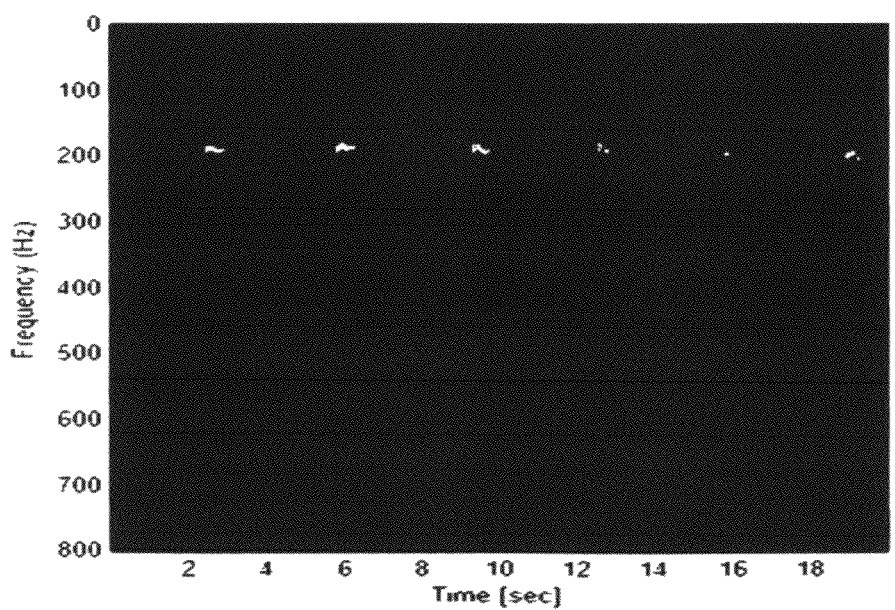
FIG. 7 shows a complete STFT image.

FIG. 7 is a complete STFT image showing the amplitude of different frequencies expressed in the respiratory signal at different times. Juxtaposition of FIG. 6 and FIG. 7 makes clear that the number of data points calculated by processing system 115 attendant to performing the method of FIG. 2 is significantly lower than the number of data points in the complete STFT image, as nonessential lines of the STFT image are skipped as a result of Steps 215 and 220, and other lines of the STFT image are only calculated in a limited frequency range as a result of frequency-bounding the lines calculated in Steps 235 and 250.

It will be appreciated by those of ordinary skill in the art that the invention can be embodied in other specific forms without departing from the spirit or essential character hereof. The present description is therefore considered in all respects to be illustrative and not restrictive. The scope of the invention is indicated by the appended claims, and all changes that come within the meaning and range of equivalents thereof are intended to be embraced therein.

What is claimed is:

1. A lightweight wheeze detection method, comprising the steps of:
   receiving by a respiratory data processing system a respiratory signal;
   calculating by the processing system noncontiguous lines of a short-time Fourier transform (STFT) image of the respiratory signal until a start line conforming to one or more wheeze peak criteria is identified;
   once a start line conforming to the wheeze peak criteria is identified, calculating by the processing system contiguous lines of the SIFT image preceding the start line and contiguous lines of the STFT image following the start line until both a preceding line and a following line not conforming to the wheeze peak criteria are identified; and,
   once both a preceding line and a following line not conforming to the wheeze peak criteria are identified, determining by the processing system using a total count of calculated lines of the STFT image conforming to the wheeze peak criteria whether a duration of a peak conforms to one or more wheeze duration criteria.

2. The method of claim 1, wherein the wheeze peak criteria comprise minimum peak frequency, minimum peak height and minimum peak width.

3. The method of claim 1, wherein conformance of a calculated line of the STFT image to the wheeze peak criteria is identified upon detecting that frequency, height and width of a highest amplitude peak in the calculated line exceed predetermined frequency, height and width thresholds, respectively.

4. The method of claim 1, wherein nonconformance of a calculated line of the STFT image with the wheeze peak criteria is identified upon detecting that one or more of frequency, height or width of a highest amplitude peak in the calculated line is below a predetermined frequency, height or width threshold, respectively.

5. The method of claim 1, wherein the wheeze duration criteria comprise a minimum wheeze duration.

6. The method of claim 1, wherein conformance to the wheeze duration criteria is determined based at least in part on a comparison of the total count with a predetermined wheeze duration threshold.

7. The method of claim 1, wherein each consecutive pair of the noncontiguous lines is separated by a predetermined number of lines of the STFT image determined in accordance with a minimum wheeze duration.

8. The method of claim 1, wherein the second calculating step comprises limiting by the processing system calculation of the contiguous lines preceding the start line and the contiguous lines following the start line to a region of each contiguous line that is within a predetermined range of a frequency of a highest amplitude peak of the start line.

9. The method of claim 1, further comprising, upon determining that the duration conforms to the wheeze duration criteria, the step of calculating by the processing system a wheeze rate.

10. The method of claim 1, further comprising, upon determining that the duration does not conform to the wheeze duration criteria, the steps of:
    skipping by the processing system a predetermined number of lines of the STFT image determined in accordance with a minimum wheeze duration; and
    re-performing the first calculating step.

11. An ambulatory health monitoring device, comprising:
    a respiratory data capture system;
    a respiratory data acquisition system communicatively coupled with the capture system;
    a respiratory data processing system communicatively coupled with the acquisition system; and
    a respiratory data output interface communicatively coupled with the processing system, wherein the processing system receives a respiratory signal from the capture system via the acquisition system, calculates noncontiguous lines of a STFT image of the respiratory signal until a start line conforming to one or more wheeze peak criteria is identified, once a start line conforming to the wheeze peak criteria is identified, calculates contiguous lines of the STFT image preceding the start line and contiguous lines of the STFT image following the start line until both a preceding line and a following line not conforming to the wheeze peak criteria are identified, once both a preceding line and a following line not conforming to the wheeze peak criteria are identified, determines using a total count of calculated lines of the STFT image conforming to the wheeze peak criteria whether a duration of a peak conforms to one or more wheeze duration criteria, upon determining that the duration conforms to the wheeze duration criteria, calculates a wheeze rate and transmits information indicative of the wheeze rate to the output interface.

12. The device of claim 11, wherein the wheeze peak criteria comprise minimum peak frequency, minimum peak height and minimum peak width.

13. The device of claim 11, wherein conformance of a calculated line of the STFT image to the wheeze peak criteria is identified upon detecting that frequency, height and width of a highest amplitude peak in the calculated line exceed predetermined frequency, height and width thresholds, respectively.

14. The device of claim 11, wherein nonconformance of a calculated line of the SIFT image with the wheeze peak criteria is identified upon detecting that one or more of frequency, height or width of a highest amplitude peak in the calculated line is below a predetermined frequency, height or width threshold, respectively.

15. The device of claim 11, wherein the wheeze duration criteria comprise a minimum wheeze duration.

16. The device of claim 11, wherein conformance of the duration to the wheeze duration criteria is determined based at least in part on a comparison of the total count with a predetermined wheeze duration threshold.

17. The device of claim 11, wherein each consecutive pair of the noncontiguous lines is separated by a predetermined number of lines of the SIFT image determined in accordance with a minimum wheeze duration.

18. The device of claim 11, wherein the processing system limits calculation of the contiguous lines preceding the start line and the contiguous lines following the start line to a region of each contiguous line that is within a predetermined range of a frequency of a highest amplitude peak of the start line.

* * * * *